(12) United States Patent
Schnarr et al.

(10) Patent No.: US 7,639,854 B2
(45) Date of Patent: Dec. 29, 2009

(54) METHOD AND SYSTEM FOR PROCESSING DATA RELATING TO A RADIATION THERAPY TREATMENT PLAN

(75) Inventors: Eric Schnarr, McFarland, WI (US); Kenneth J. Ruchala, Madison, WI (US); Gustavo H. Olivera, Madison, WI (US); Weiguo Lu, Madison, WI (US); Jeffrey M. Kapatoes, Madison, WI (US); Jason Haimerl, Lake Mills, WI (US); John H. Hughes, Madison, WI (US); Thomas R. Mackie, Verona, WI (US)

(73) Assignee: TomoTherapy Incorporated, Madison, WI (US)

( * ) Notice: Subject to any disclaimer, the term of this patent is extended or adjusted under 35 U.S.C. 154(b) by 192 days.

(21) Appl. No.: 11/459,108

(22) Filed: Jul. 21, 2006

(65) Prior Publication Data

US 2007/0041497 A1 Feb. 22, 2007

Related U.S. Application Data

(60) Provisional application No. 60/701,580, filed on Jul. 22, 2005, provisional application No. 60/726,548, filed on Oct. 14, 2005.

(51) Int. Cl.
*G06K 9/00* (2006.01)
*A61B 5/05* (2006.01)
(52) U.S. Cl. .................. 382/128; 382/131; 382/132; 600/427

(58) Field of Classification Search ................ 382/128, 382/131, 132; 600/427
See application file for complete search history.

(56) References Cited

U.S. PATENT DOCUMENTS 3,949,265 A    4/1976    Holl
(Continued)

FOREIGN PATENT DOCUMENTS

CA    2091275    9/1993
(Continued)

OTHER PUBLICATIONS

PCT/US06/28537 International Search Report and Written Opinion mailed Sep. 26, 2007.
(Continued)

*Primary Examiner*—John B Strege
(74) *Attorney, Agent, or Firm*—Michael Best & Friedrich LLP (57) ABSTRACT

A system and method of automatically processing data relating to a radiation therapy treatment plan. The method includes the acts of acquiring image data of a patient, generating a treatment plan for the patient based at least in part on the image data, the treatment plan including a calculated radiation dose to be delivered to the patient, acquiring an on-line image of the patient in substantially a treatment position, delivering at least a portion of the calculated radiation dose to the patient, and automatically recalculating the radiation dose received by the patient.

56 Claims, 6 Drawing Sheets

U.S. PATENT DOCUMENTS

| | | |
|---|---|---|
| 3,964,467 A | 6/1976 | Rose |
| 4,006,422 A | 2/1977 | Schriber |
| 4,032,810 A | 6/1977 | Eastham et al. |
| 4,149,081 A | 4/1979 | Seppi |
| 4,181,894 A | 1/1980 | Pottier |
| 4,189,470 A | 2/1980 | Rose |
| 4,208,185 A | 6/1980 | Sawai et al. |
| 4,273,867 A | 6/1981 | Lin et al. |
| 4,314,180 A | 2/1982 | Salisbury |
| 4,335,465 A | 6/1982 | Christiansen et al. |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,124,658 A | 6/1992 | Adler |
| 5,210,414 A | 5/1993 | Wallace et al. |
| 5,250,388 A | 10/1993 | Schoch et al. |
| 5,317,616 A | 5/1994 | Swerdloff et al. |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,523,578 A | 6/1996 | Herskovic |
| 5,528,650 A | 6/1996 | Swerdloff et al. |
| 5,548,627 A | 8/1996 | Swerdloff et al. |
| 5,576,602 A | 11/1996 | Hiramoto et al. |
| 5,578,909 A | 11/1996 | Billen |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,834,454 A | 11/1998 | Kitano et al. |
| 5,836,905 A | 11/1998 | Lemelson et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,152,599 A | 11/2000 | Salter |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |
| 6,218,675 B1 | 4/2001 | Akiyama et al. |
| 6,222,905 B1 | 4/2001 | Yoda et al. |
| 6,241,670 B1 | 6/2001 | Nambu |
| 6,242,747 B1 | 6/2001 | Sugitani et al. |
| 6,264,825 B1 | 7/2001 | Blackburn et al. |
| 6,265,837 B1 | 7/2001 | Akiyama et al. |
| 6,279,579 B1 | 8/2001 | Riaziat et al. |
| 6,291,823 B1 | 9/2001 | Doyle et al. |
| 6,316,776 B1 | 11/2001 | Hiramoto et al. |
| 6,319,469 B1 | 11/2001 | Mian et al. |
| 6,322,249 B1 | 11/2001 | Wofford et al. |

| Patent No. | Date | Inventor |
|---|---|---|
| 6,331,194 B1 | 12/2001 | Sampayan et al. |
| 6,345,114 B1 | 2/2002 | Mackie et al. |
| 6,360,116 B1 | 3/2002 | Jackson, Jr. et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,407,505 B1 | 6/2002 | Bertsche |
| 6,417,178 B1 | 7/2002 | Klunk et al. |
| 6,424,856 B1 | 7/2002 | Vilsmeier et al. |
| 6,428,547 B1 | 8/2002 | Vilsmeier et al. |
| 6,433,349 B2 | 8/2002 | Akiyama et al. |
| 6,438,202 B1 | 8/2002 | Olivera et al. |
| 6,455,844 B1 | 9/2002 | Meyer |
| 6,462,490 B1 | 10/2002 | Matsuda et al. |
| 6,465,957 B1 | 10/2002 | Whitham et al. |
| 6,466,644 B1 | 10/2002 | Hughes et al. |
| 6,469,058 B1 | 10/2002 | Grove et al. |
| 6,472,834 B2 | 10/2002 | Hiramoto et al. |
| 6,473,490 B1 | 10/2002 | Siochi |
| 6,475,994 B2 | 11/2002 | Tomalia et al. |
| 6,482,604 B2 | 11/2002 | Kwon |
| 6,484,144 B2 | 11/2002 | Martin et al. |
| 6,487,274 B2 | 11/2002 | Bertsche |
| 6,493,424 B2 | 12/2002 | Whitham |
| 6,497,358 B1 | 12/2002 | Walsh |
| 6,498,011 B2 | 12/2002 | Hohn et al. |
| 6,500,343 B2 | 12/2002 | Siddiqi |
| 6,504,899 B2 | 1/2003 | Pugachev et al. |
| 6,510,199 B1 | 1/2003 | Hughes et al. |
| 6,512,942 B1 | 1/2003 | Burdette et al. |
| 6,516,046 B1 | 2/2003 | Frohlich et al. |
| 6,527,443 B1 | 3/2003 | Vilsmeier et al. |
| 6,531,449 B2 | 3/2003 | Khojasteh et al. |
| 6,535,837 B1 | 3/2003 | Schach Von Wittenau |
| 6,552,338 B1 | 4/2003 | Doyle |
| 6,558,961 B1 | 5/2003 | Sarphie et al. |
| 6,560,311 B1 | 5/2003 | Shepard et al. |
| 6,562,376 B2 | 5/2003 | Hooper et al. |
| 6,584,174 B2 | 6/2003 | Schubert et al. |
| 6,586,409 B1 | 7/2003 | Wheeler |
| 6,605,297 B2 | 8/2003 | Nadachi et al. |
| 6,611,700 B1 | 8/2003 | Vilsmeier et al. |
| 6,617,768 B1 | 9/2003 | Hansen |
| 6,618,467 B1 | 9/2003 | Ruchala et al. |
| 6,621,889 B1 | 9/2003 | Mostafavi |
| 6,633,686 B1 | 10/2003 | Bakircioglu et al. |
| 6,634,790 B1 | 10/2003 | Salter, Jr. |
| 6,636,622 B2 | 10/2003 | Mackie et al. |
| 6,637,056 B1 | 10/2003 | Tybinkowski et al. |
| 6,646,383 B2 | 11/2003 | Bertsche et al. |
| 6,653,547 B2 | 11/2003 | Akamatsu |
| 6,661,870 B2 | 12/2003 | Kapatoes et al. |
| 6,688,187 B1 | 2/2004 | Masquelier |
| 6,690,965 B1 | 2/2004 | Riaziat et al. |
| 6,697,452 B2 | 2/2004 | Xing |
| 6,705,984 B1 | 3/2004 | Angha |
| 6,713,668 B2 | 3/2004 | Akamatsu |
| 6,713,976 B1 | 3/2004 | Zumoto et al. |
| 6,714,620 B2 | 3/2004 | Caflisch et al. |
| 6,714,629 B2 | 3/2004 | Vilsmeier |
| 6,716,162 B2 | 4/2004 | Hakamata |
| 6,723,334 B1 | 4/2004 | McGee et al. |
| 6,741,674 B2 | 5/2004 | Lee |
| 6,760,402 B2 | 7/2004 | Ghelmansarai |
| 6,774,383 B2 | 8/2004 | Norimine et al. |
| 6,787,771 B2 | 9/2004 | Garty et al. |
| 6,787,983 B2 | 9/2004 | Yamanobe et al. |
| 6,788,764 B2 | 9/2004 | Saladin et al. |
| 6,792,073 B2 | 9/2004 | Deasy et al. |
| 6,796,164 B2 | 9/2004 | McLoughlin et al. |
| 6,800,866 B2 | 10/2004 | Amemiya et al. |
| 6,822,244 B2 | 11/2004 | Beloussov et al. |
| 6,822,247 B2 | 11/2004 | Sasaki |
| 6,838,676 B1 | 1/2005 | Jackson |
| 6,842,502 B2 | 1/2005 | Jaffray et al. |
| 6,844,689 B1 | 1/2005 | Brown et al. |
| 6,871,171 B1 | 3/2005 | Agur et al. |
| 6,873,115 B2 | 3/2005 | Sagawa et al. |
| 6,873,123 B2 | 3/2005 | Marchand et al. |
| 6,878,951 B2 | 4/2005 | Ma |
| 6,882,702 B2 | 4/2005 | Luo |
| 6,882,705 B2 | 4/2005 | Egley et al. |
| 6,888,326 B2 | 5/2005 | Amaldi et al. |
| 6,889,695 B2 | 5/2005 | Pankratov et al. |
| 6,907,282 B2 | 6/2005 | Siochi |
| 6,922,455 B2 | 7/2005 | Jurczyk et al. |
| 6,929,398 B1 | 8/2005 | Tybinkowski et al. |
| 6,936,832 B2 | 8/2005 | Norimine et al. |
| 6,955,464 B1 | 10/2005 | Tybinkowski et al. |
| 6,963,171 B2 | 11/2005 | Sagawa et al. |
| 6,974,254 B2 | 12/2005 | Paliwal et al. |
| 6,984,835 B2 | 1/2006 | Harada |
| 6,990,167 B2 | 1/2006 | Chen |
| 7,015,490 B2 | 3/2006 | Wang et al. |
| 7,046,762 B2 | 5/2006 | Lee |
| 7,051,605 B2 | 5/2006 | Lagraff et al. |
| 7,060,997 B2 | 6/2006 | Norimine et al. |
| 7,077,569 B1 | 7/2006 | Tybinkowski et al. |
| 7,081,619 B2 | 7/2006 | Bashkirov et al. |
| 7,084,410 B2 | 8/2006 | Beloussov et al. |
| 7,087,200 B2 | 8/2006 | Taboas et al. |
| 7,112,924 B2 | 9/2006 | Hanna |
| 7,130,372 B2 | 10/2006 | Kusch et al. |
| 7,154,991 B2 | 12/2006 | Earnst et al. |
| 7,186,986 B2 | 3/2007 | Hinderer et al. |
| 7,186,991 B2 | 3/2007 | Kato et al. |
| 7,203,272 B2 | 4/2007 | Chen |
| 7,209,547 B2 | 4/2007 | Baier et al. |
| 7,221,733 B1 | 5/2007 | Takai et al. |
| 7,252,307 B2 | 8/2007 | Kanbe et al. |
| 7,257,196 B2 | 8/2007 | Brown et al. |
| 7,391,026 B2 | 6/2008 | Trinkaus et al. |
| 2002/0007918 A1 | 1/2002 | Owen et al. |
| 2002/0077545 A1 | 6/2002 | Takahashi et al. |
| 2002/0080915 A1 | 6/2002 | Frohlich |
| 2002/0085668 A1 | 7/2002 | Blumhofer et al. |
| 2002/0091314 A1 | 7/2002 | Schlossbauer et al. |
| 2002/0115923 A1 | 8/2002 | Erbel |
| 2002/0120986 A1 | 9/2002 | Erbel et al. |
| 2002/0122530 A1 | 9/2002 | Erbel et al. |
| 2002/0136439 A1 | 9/2002 | Ruchala et al. |
| 2002/0150207 A1 | 10/2002 | Kapatoes et al. |
| 2002/0187502 A1 | 12/2002 | Waterman et al. |
| 2002/0193685 A1 | 12/2002 | Mate et al. |
| 2003/0007601 A1 | 1/2003 | Jaffray et al. |
| 2003/0031298 A1 | 2/2003 | Xing |
| 2003/0086527 A1 | 5/2003 | Speiser et al. |
| 2003/0105650 A1 | 6/2003 | Lombardo et al. |
| 2003/0174872 A1 | 9/2003 | Chalana et al. |
| 2004/0010418 A1 | 1/2004 | Buonocore et al. |
| 2004/0068182 A1 | 4/2004 | Misra |
| 2004/0116804 A1 | 6/2004 | Mostafavi |
| 2004/0165696 A1 | 8/2004 | Lee |
| 2004/0202280 A1 | 10/2004 | Besson |
| 2004/0230115 A1 | 11/2004 | Scarantino et al. |
| 2004/0254492 A1 | 12/2004 | Zhang et al. |
| 2004/0254773 A1 | 12/2004 | Zhang et al. |
| 2004/0264640 A1 | 12/2004 | Myles |
| 2005/0013406 A1 | 1/2005 | Dyk et al. |
| 2005/0031181 A1 | 2/2005 | Bi et al. |
| 2005/0080332 A1 | 4/2005 | Shiu et al. |
| 2005/0096515 A1 | 5/2005 | Geng |
| 2005/0123092 A1 | 6/2005 | Mistretta et al. |
| 2005/0143965 A1 | 6/2005 | Failla et al. |
| 2005/0180544 A1 | 8/2005 | Sauer et al. |

| | | |
|---|---|---|
| 2005/0197564 A1 | 9/2005 | Dempsey |
| 2005/0251029 A1* | 11/2005 | Khamene et al. ............ 600/427 |
| 2006/0074292 A1 | 4/2006 | Thomson et al. |
| 2006/0083349 A1 | 4/2006 | Harari et al. |
| 2006/0100738 A1 | 5/2006 | Alsafadi et al. |
| 2006/0133568 A1 | 6/2006 | Moore |
| 2006/0193429 A1 | 8/2006 | Chen |
| 2006/0193441 A1 | 8/2006 | Cadman |
| 2006/0285639 A1 | 12/2006 | Olivera et al. |
| 2007/0041494 A1 | 2/2007 | Ruchala et al. |
| 2007/0041495 A1 | 2/2007 | Olivera et al. |
| 2007/0041497 A1 | 2/2007 | Schnarr et al. |
| 2007/0041498 A1 | 2/2007 | Olivera et al. |
| 2007/0041499 A1 | 2/2007 | Lu et al. |
| 2007/0041500 A1 | 2/2007 | Olivera et al. |
| 2007/0043286 A1 | 2/2007 | Lu et al. |
| 2007/0076846 A1 | 4/2007 | Ruchala et al. |
| 2007/0088573 A1 | 4/2007 | Ruchala et al. |
| 2007/0104316 A1 | 5/2007 | Ruchala et al. |
| 2007/0127623 A1 | 6/2007 | Goldman et al. |
| 2007/0189591 A1 | 8/2007 | Lu et al. |
| 2007/0195922 A1 | 8/2007 | Mackie et al. |
| 2007/0195929 A1 | 8/2007 | Ruchala et al. |
| 2007/0195930 A1 | 8/2007 | Kapatoes et al. |
| 2007/0201613 A1 | 8/2007 | Lu et al. |
| 2007/0211857 A1 | 9/2007 | Urano et al. |

FOREIGN PATENT DOCUMENTS

| | | |
|---|---|---|
| CA | 2180227 | 12/1996 |
| WO | WO 03/076003 | 9/2003 |
| WO | 2004057515 | 7/2004 |

OTHER PUBLICATIONS

Ronald D. Rogus et al., "Accuracy of a Photogrammetry-Based Patient Positioning and Monitoring System for Radiation Therapy," Medical Physics, vol. 26, Issue 5, May 1999.

D. Rueckert et al., "Nonrigid Registration Using Free-Form Deformations: Application to Breast MR Images," IEEE Transactions on Medical Imaging, vol. 18, No. 8, Aug. 1999.

Yuan-Nan Young, "Registration-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001. (Note: the title of the periodical and the date listed are from the International Search Report, however they do not appear on the article itself.).

Ruchala, Kenneth, et al., "Adaptive IMRT with Tomotherapy", RT Image, vol. 14 No. 25, pp. 14-18, Jun. 18, 2001.

Marcelo Bertalmio, et al., "Morphing Active Contours", IEEE Transactions on Pattern Analysis and Machine Intelligence, vol. 22, No. 7, pp. 733-737, Jul. 2000.

Lu, W., et al., "Automatic Re-Contouring in 4D Radiology", Physical Medical Biology, Mar. 7, 2006, 51(5): 1077-99.

Lu, W., et al., 2004 Automatic Re-Contouring for 4-D Planning and Adaptive Radiotherapy, The 90th RSNA Meeting, Chicago, Illinois, (abstract: Radiology 227 (p) 543).

Lu, W., et al., 2004 Automatic Re-Contouring Regions of Interest Based on Deformable Registration and Surface Reconstruction, AAPM 2004, (abstract: Medical Physics 31, 1845-6).

* cited by examiner

METHOD AND SYSTEM FOR PROCESSING DATA RELATING TO A RADIATION THERAPY TREATMENT PLAN

RELATED APPLICATIONS

This application claims priority to U.S. Provisional Patent Application No. 60/701,580, filed on Jul. 22, 2005, titled SYSTEM AND METHOD FOR FEEDBACK GUIDED QUALITY ASSURANCE AND ADAPTATIONS TO RADIATION THERAPY TREATMENT, and to U.S. Provisional Patent Application No. 60/726,548, filed on Oct. 14, 2005, titled "METHOD AND INTERFACE FOR ADAPTIVE RADIATION THERAPY", the entire contents of which are incorporated herein by reference.

BACKGROUND

Over the past decades improvements in computers and networking, radiation therapy treatment planning software, and medical imaging modalities (CT, MRI, US, and PET) have been incorporated into radiation therapy practice. These improvements have led to the development of image guided radiation therapy ("IGRT"). IGRT is radiation therapy that uses cross-sectional images of the patient's internal anatomy to better target the radiation dose in the tumor while reducing the radiation exposure to healthy organs. The radiation dose delivered to the tumor is controlled with intensity modulated radiation therapy ("IMRT"), which involves changing the size, shape, and intensity of the radiation beam to conform to the size, shape, and location of the patient's tumor. IGRT and IMRT lead to improved control of the tumor while simultaneously reducing the potential for acute side effects due to irradiation of healthy tissue surrounding the tumor.

IMRT is becoming the standard of care in several countries. However, in many situations, IMRT is not used to treat a patient due to time, resources, and billing constraints. Daily images of the patient can be used to guarantee that the high gradients generated by IMRT plans are located on the correct position for patient treatment. Also these images can provide necessary information to adapt the plan online or offline if needed.

It is commonly known in the field of radiation therapy that there are many sources of uncertainty and change that can occur during a course of a patient's treatment. Some of these sources represent random errors, such as small differences in a patient's setup position each day. Other sources are attributable to physiological changes, which might occur if a patient's tumor regresses or the patient loses weight during therapy. A third possible category regards motion. Motion can potentially overlap with either of the other categories, as some motion might be more random and unpredictable, such as a patient coughing or passing gas, whereas other motion can be more regular, such as breathing motion, sometimes.

SUMMARY

In radiation therapy, uncertainties can affect the quality of a patient's treatment. For example, when delivering a treatment dose to a target region, it is standard practice to also treat a high-dose "margin" region about the target. This helps ensure that the target receives the desired dose, even if its location changes during the course of the treatment, or even during a single fraction. The less definite a target's location, the larger the margins that typically need to be used.

Adaptive radiation therapy generally refers to the concept of using feedback during the course of radiation therapy treatment to improve future treatments. Feedback can be used in off-line adaptive therapy processes and on-line adaptive therapy processes. Off-line adaptive therapy processes occur while the patient is not being treated, such as in between treatment fractions. In one version of this, during each fraction, a new CT image of the patient is acquired before or after each of the fractions. After the images are acquired from the first few treatment fractions, the images are evaluated to determine an effective envelope of the multi-day locations of target structures. A new plan can then be developed to better reflect the range of motion of the target structure, rather than using canonical assumptions of motion. A more complex version of off-line adaptive therapy is to recalculate the delivered dose after each fraction and accumulate these doses, potentially utilizing deformation techniques, during this accumulation to account for internal motion. The accumulated dose can then be compared to the planned dose, and if any discrepancies are noted, subsequent fractions can be modified to account for the changes.

On-line adaptive therapy processes typically occur while the patient is in the treatment room, and potentially, but not necessarily, during a treatment delivery. For example, some radiation therapy treatment systems are equipped with imaging systems, such as on-line CT or X-Ray systems. These systems can be used prior to treatment to validate or adjust the patient's setup for the treatment delivery. The imaging systems may also be used to adapt the treatment during the actual treatment delivery. For example, an imaging system potentially can be used concurrently with treatment to modify the treatment delivery to reflect changes in patient anatomy.

One aspect of the present invention is to disclose new opportunities for the application of adaptive therapy techniques, and additional aspects are to present novel methods for adaptive therapy. In particular, adaptive therapy has typically focused on feedback to modify a patient's treatment, but the present invention focuses on adaptive therapy processes being used in a quality assurance context. This is particularly true in the context of whole-system verification.

For example, a detector can be used to collect information indicating how much treatment beam has passed through the patient, from which the magnitude of the treatment output can be determined as well as any radiation pattern that was used for the delivery. The benefit of this delivery verification process is that it enables the operator to detect errors in the machine delivery, such as an incorrect leaf pattern or machine output.

However, validating that the machine is functioning properly does not itself ensure proper delivery of a treatment plan, as one also needs to validate that the external inputs used to program the machine are effective and consistent. Thus, one aspect of the invention includes the broader concept of an adaptive-type feedback loop for improved quality assurance of the entire treatment process. In this aspect, the invention includes the steps of positioning the patient for treatment and using a method for image-guidance to determine the patient's position, repositioning the patient as necessary for treatment based upon the image-guidance, and beginning treatment. Then, either during or after treatment, recalculating the patient dose and incorporating the patient image information that had been collected before or during treatment. After completion of these steps, quality assurance data is collected to analyze the extent to which the delivery was not only performed as planned, but to validate that the planned delivery is reasonable in the context of the newly available data. In this regard, the concept of feedback is no longer being used to indicate changes to the treatment based on changes in the patient or delivery, but to validate the original delivery itself.

As an example, it is possible that a treatment plan might be developed for a patient, but that the image used for planning became corrupted, such as by applying an incorrect density calibration. In this case, the treatment plan will be based upon incorrect information, and might not deliver the correct dose to the patient. Yet, many quality assurance techniques will not detect this error because they will verify that the machine is operating as instructed, rather than checking whether the instructions to the machine are based on correct input information. Likewise, some adaptive therapy techniques could be applied to this delivery, but if the calibration problem of this example persisted, then the adapted treatments would suffer from similar flaws.

There are a number of processes that can be used to expand the use of feedback for quality assurance purposes. For example, in one embodiment, this process would include the delivery verification techniques described above. The validation of machine performance that these methods provide is a valuable component of a total-system quality assurance toolset. Moreover, the delivery verification processes can be expanded to analyze other system errors, such as deliveries based on images with a truncated field-of-view.

In one embodiment, the invention provides a method of automatically processing data relating to a radiation therapy treatment plan. The method comprises the acts of acquiring image data of a patient, generating a treatment plan for the patient based at least in part on the image data, the treatment plan including a calculated radiation dose to be delivered to the patient, acquiring an on-line image of the patient in substantially a treatment position, delivering at least a portion of the calculated radiation dose to the patient, and automatically recalculating the radiation dose received by the patient.

In another embodiment, the invention provides a method of automatically processing data relating to a radiation therapy treatment plan. The method comprises the acts of acquiring image data of a patient, generating a treatment plan for the patient based at least in part on the image data, the treatment plan including a calculated radiation dose to be delivered to the patient, inputting new data relating to radiation therapy treatment, the data not included in the treatment plan, delivering at least a portion of the calculated radiation dose to the patient, and automatically recalculating the radiation dose received by the patient.

In yet another embodiment, the invention provides a system for automatically processing data relating to a radiation therapy treatment plan. The system includes a radiation therapy treatment device and a software program. The radiation therapy treatment device includes a computer processor, the radiation therapy treatment device operable to deliver radiation to a patient according to a treatment plan. The software program is stored in a computer readable medium accessible by the computer processor and is operable to acquire image data of a patient, generate a treatment plan for the patient based at least in part on the image data, the treatment plan including a calculated radiation dose to be delivered to the patient, acquire an on-line image of the patient in substantially a treatment position, deliver at least a portion of the calculated radiation dose to the patient, and automatically recalculate the radiation dose received by the patient.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
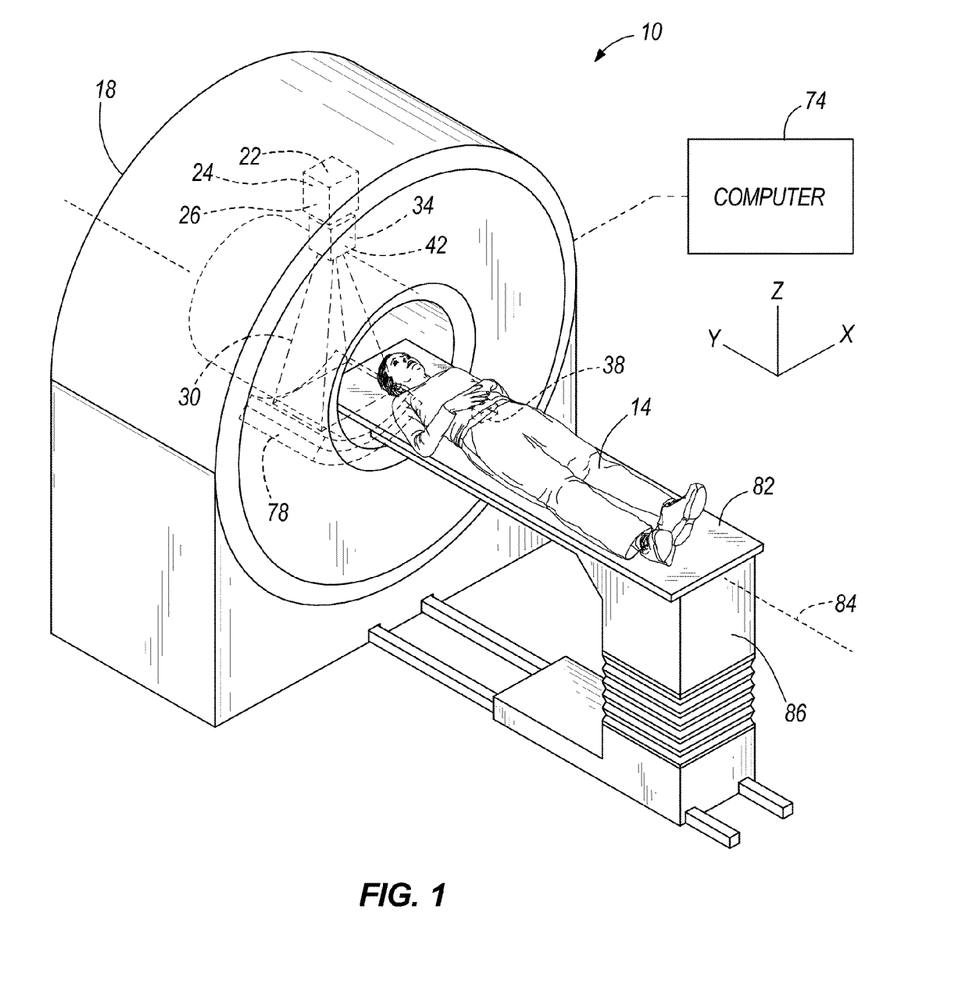
FIG. 1 is a perspective view of a radiation therapy treatment system.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. The target 38 may also include a margin around or partially around the target. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
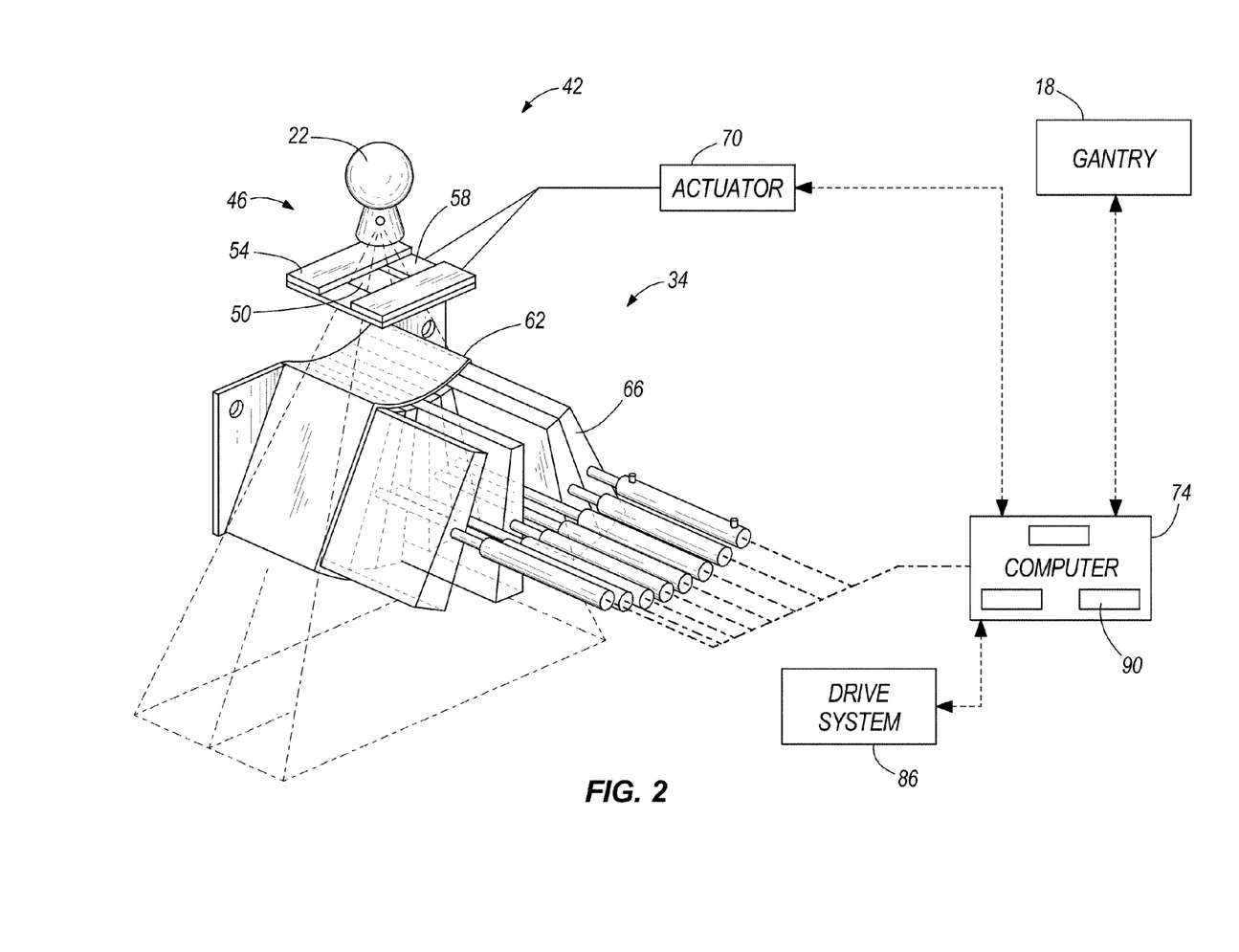
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support is not limited to having to support the entire patient's body. The system 10 also can include a drive system 86 operable to manipulate the position of the couch 82. The drive system 86 can be controlled by the computer 74.

Figure 3:
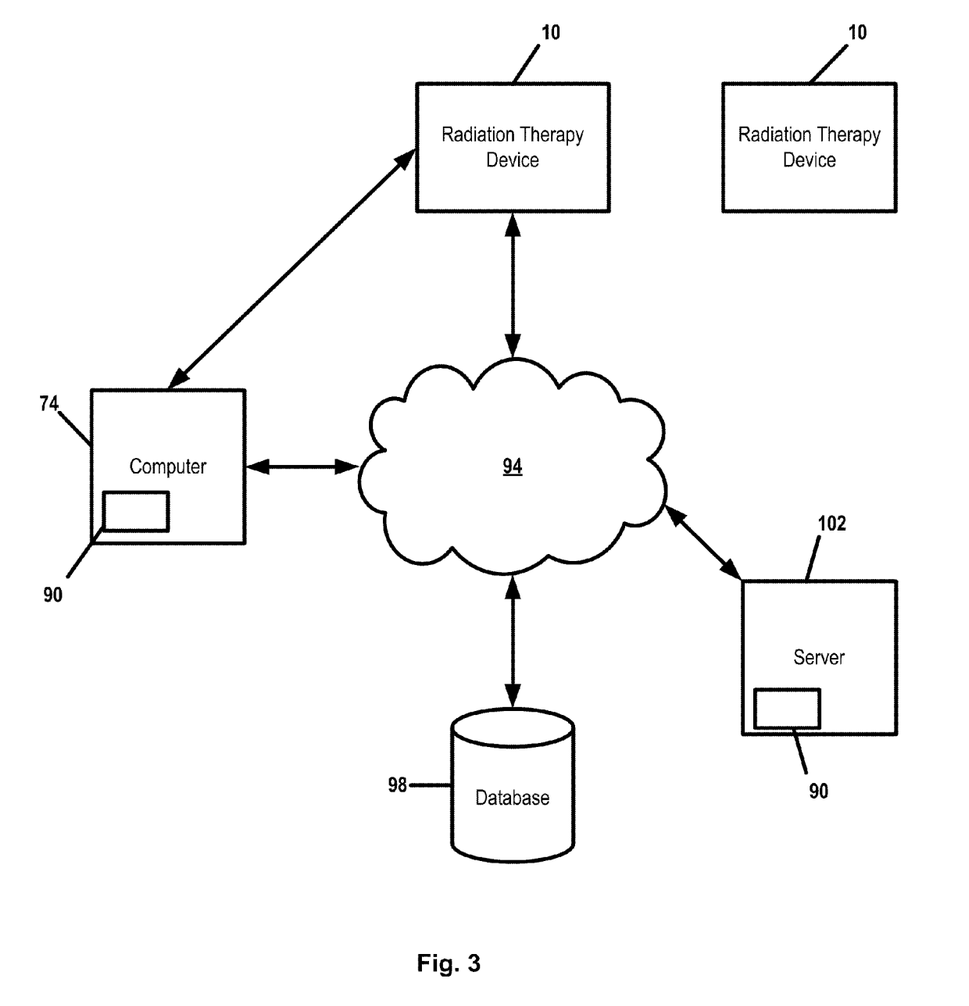
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The software program(s) 90 is operable to receive data from external software programs and hardware and it is noted that data may be input to the software program(s) 90.

The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine ("DICOM") protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
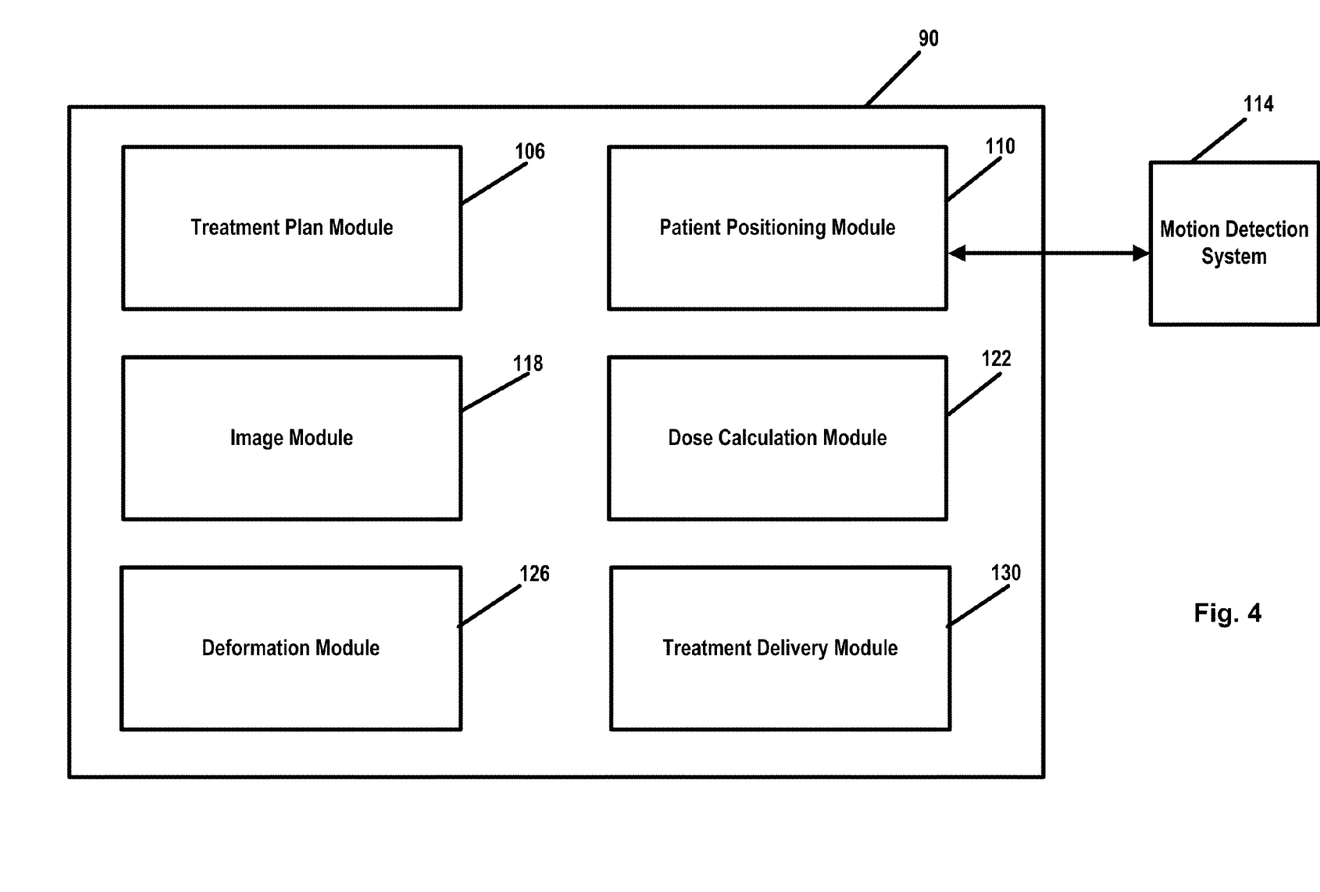
FIG. 4 is a schematic diagram of a software program used in the radiation therapy treatment system.

One aspect of the invention is a method for facilitating the adaptive and quality assurance processes and to render the process more efficient. This is particularly important since even procedures that might seem simple and fast for one or two images might become tedious and impractical for cases with large numbers of daily images. The software program 90 can perform many of the processes either automatically or semi-automatically. In one implementation, the automation includes both individual steps, and the process as a whole. For example, after collecting a daily image, such as an on-line CT, the patient can be automatically positioned and/or registered (subject to clinical review) and the predicted radiation dose can be automatically calculated on the daily image to indicate the radiation dose that would be delivered for the specified patient position.

Once radiation therapy treatment delivery commences, exit data can be automatically collected to analyze the treatment, and can be used to abort or alter the treatment if significant discrepancies are detected. Additional images or patient monitoring data can be acquired during treatment to detect any changes in patient position or anatomy. After treatment, the radiation dose can be automatically reconstructed based upon the relevant patient images and the treatment monitoring data (this can also include automatic processing of steps such as couch replacement and calibration curve selection).

The patient images can be automatically registered to the planning images using deformation techniques so as to provide updated daily contours and a means for accumulating multi-day doses accurately. The doses can be automatically accumulated, and metrics can be automatically applied to determine the effect of the delivery on the patient and to see whether the delivery falls within clinical tolerances (e.g., NTCP, TCP, EUD, BED, etc.) If any discrepancies are noted in the treatment, the medical personnel can be automatically notified to review the treatment. If any changes in current or future treatments are desired, new plans can be automatically generated that would compensate for the measured discrepancies.

Another aspect of automating adaptive and quality assurance processes is that the user can define macros that customize the automation process. Portions of this process can be replaced or modified, and new or revised metrics for notification can be implemented throughout the process.

The automatic processing is performed by the software program 90 and/or additional software or hardware. The software program 90 includes a plurality of modules that communicate with one another to perform functions of the radiation therapy treatment process. The various modules communicate with one another to automatically analyze data related to the radiation therapy treatment process.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38, image data, and other patient data. Multiple targets 38 may be present and included in the same treatment plan.

The software program 90 also includes a patient positioning module 110 operable to position and align the patient 14 with respect to the isocenter of the gantry 18 for a particular treatment fraction. While the patient is on the couch 82, the patient positioning module 110 acquires an image of the patient 14 and compares the current position of the patient 14 to the position of the patient in a planning or previously acquired image. If the patient's position needs to be adjusted, the patient positioning module 110 provides instructions to the drive system 86 to move the couch 82 or the patient 14 can be manually moved to the new position. In one construction, the patient positioning module 110 can receive data from lasers positioned in the treatment room to provide patient position data with respect to the isocenter of the gantry 18. Based on the data from the lasers, the patient positioning module 110 provides instructions to the drive system 86, which moves the couch 82 to achieve proper alignment of the patient 14 with respect to the gantry 18. It is noted that devices and systems, other than lasers, can be used to provide data to the patient positioning module 110 to assist in the alignment process.

The patient positioning module 110 also is operable to detect and/or monitor patient motion during treatment. The patient positioning module 110 may communicate with and/ or incorporate a motion detection system 114, such as x-ray, in-room CT, laser positioning devices, camera systems, spirometers, ultrasound, tensile measurements, chest bands, and the like. The patient motion can be irregular or unexpected, and does not need to follow a smooth or reproducible path.

The software program 90 also includes an image module 118 operable to acquire images of at least a portion of the patient 14. The image module 118 can instruct the on-board image device, such as a CT imaging device to acquire images of the patient 14 before treatment commences, during treatment, and after treatment according to desired protocols. Other off-line imaging devices or systems may be used to acquire pre-treatment images of the patient 14, such as non-quantitative CT, MRI, PET, SPECT, ultrasound, transmission imaging, fluoroscopy, RF-based localization, and the like. The other imaging devices may be remote from the system 10 and not on-board the system 10. The acquired image(s) can be used for registration of the patient 14 and/or to generate a deformation map to identify the differences between one or more of the planning images, the pre-treatment images, and/or the reference images. The acquired images also can be used to determine or predict a radiation dose to be delivered to the patient 14. The acquired images also can be used to determine a radiation dose that the patient 14 received during the prior treatments. The image module 118 also is operable to acquire images of at least a portion of the patient 14 while the patient is receiving treatment to determine a radiation dose that the patient 14 is receiving in real-time.

The software program 90 also includes a radiation dose calculation module 122 operable to receive patient data (real-time and historic), patient image data (e.g., the planning images, the pre-treatment images, and/or other reference images), patient position data, anatomical position data, and system or machine data. The dose calculation module 122 is also operable to calculate a radiation dose to be delivered to the patient 14 and/or to determine the amount of radiation dose that was delivered to the patient 14 during one or more treatments. The radiation dose calculation module 122 also is operable to recalculate radiation dose to be delivered to the patient 14 in the current and also future treatments of the treatment plan. In one aspect, the radiation dose is recalculated for those treatments based on a deformable registration of one or more images of the patient 14.

As one example, the dose delivered to the patient 14 can be evaluated using a gamma index. The gamma (γ) index is used to simultaneously test both percent dose difference in plateau regions and distance to agreement in high gradient regions. Percent dose difference is a useful metric in regions of uniform dose—the plateau regions—but is not appropriate for high gradient regions. Distance to agreement is a more appropriate metric for high dose gradient regions. The γ index was introduced by Low et. al. (Daniel A. Low, William B. Harms, Sasa Mutic, James A. Purdy, "A technique for the quantitative evaluation of dose distributions," Medical Physics, Volume 25, Issue 5, May 1998, pp. 656-661.) Given a percent-dose/distance criterion (e.g., 5%-3 mm) γ is calculated for every sample point in a dose profile (1-D), image (2-D), or volume (3-D). Wherever γ<=1 the criteria is met; where γ>1 the criteria is not met.

As another example, the dose delivered to the patient 14 can be evaluated using a xi index. The xi (ξ) index is a generalization of the procedure outlined by Van Dyk et al. (1993) for treatment planning commissioning. With this method, both distributions be compared in their gradient components first, followed by a dose-difference (ΔD) and distance-to-agreement (DTA) analysis. Since there are two dose distributions and two dose gradient classifications (high dose gradient or low dose gradient), there are four possible combinations. Given $v_{ref}$ is the voxel in the reference distribution and $v_{eval}$ is the voxel in the evaluation distribution, these combinations are:

$v_{ref}$ is high dose gradient, $v_{eval}$ is high dose gradient $v_{ref}$ is high dose gradient, $v_{eval}$ is low dose gradient $v_{ref}$ is low dose gradient, $v_{eval}$ is high dose gradient $v_{ref}$ is low dose gradient, $v_{eval}$ is low dose gradient In the proposed comparison tool, for regions in which both the reference and comparison distributions have low dose gradients, ΔD values are obtained. For all other cases, DTA analysis is done. The gradient comparison accounts for the fact that there may be a complete mismatch of dose gradients between the reconstructed and planned distributions. Once ΔD and DTA values are obtained, a numerical index for each voxel can be found that is similar the gamma index proposed by Low et al. (1998). The numerical index ξ is found by the following:

$$\xi_{high\ gradient\ voxels} = \left| \frac{DTA}{DTA\ tolerance} \right|, \quad (1)$$

$$\xi_{low\ gradient\ voxels} = \left| \frac{\Delta D}{\Delta D\ tolerance} \right|$$

A ξ value of one or less is considered acceptable. Though a volume can have both high and low gradient voxels, this approach is amenable to averaging or display since the ξ values are dimensionless.

The dose calculation module 122 can determine the effect that the location and/or movement of the patient had on the delivery of the prescribed radiation dose using 4D CT images, motion-correction 3D images, or other patient motion tracking methods. "4D CT" images are a collection of 3D image volumes that each represent a "phase" of a motion pattern, such as breathing. The dose calculation module 122 can recalculate dose more accurately on one of these volumes.

The dose calculation module 122 can determine the amount of radiation dose that was delivered to the patient 14 by using data from the motion detection system 114 to identify the phase that the patient was in at any given time, and recalculating the radiation dose for each time in the phase of the 4D CT image that best matches the patient's instantaneous position. Based on a better understanding of the amount of radiation dose that the patient is actually receiving, the medical personnel can make adjustments to the treatment plan, patient position/registration, dose amount, dose distribution, as well as other parameters and system settings while the patient is receiving the treatment. Dose calculations can also be performed on updated 4D CT images, as well as other types of 4D images, such as 4D PET or 4D MRI, that are acquired before or during treatment.

The dose calculation module 122 can provide information to the medical personnel related to the biological effect that the radiation dose has on the patient 14. The dose calculation module 122 can determine the biological effects of radiation on tissues, tumors, and organs based on the amount of radiation dose that the patient 14 has received and/or on the patient's registration. Based on the biological effects, the medical personnel can adjust the patient 14, the system settings, or make other adjustments in the treatment plan. The biological information can be incorporated in the patient registration process to identify a preferred position for the patient 14 that results in a delivered dose with a preferred biological effect.

The dose calculation module 122 can utilize data related to the radiation dose actually delivered and the biological effects of the radiation dose delivered to apply a biological model that relates the clinical dose to the patient effect. The net radiation dose delivered (accumulated using deformation techniques) can be used to estimate the biological effect that would result from continuing the treatment, and likewise, possible alternatives for adapting the treatment would be evaluated for a preferred biological effect. The resulting fractionation schedule, dose distribution, and plans can reflect this culmination of information.

The software program 90 also includes a deformation module 126 operable to receive data, such as image data from the image module 118 and the treatment planning module 106 and other patient and system data from the treatment plan module 106 to generate a deformation map of the images. The deformation module 126 can use deformation techniques to determine an accumulation of radiation dose for all of the delivered treatments.

A deformation map can be utilized to relate a plurality of images for dose calculation purposes. For example, a deformation map can relate a planning image that is useful for dose calculation, and an on-line image, which has qualitative value but less direct utility for dose calculation. This relationship can then be used to "remap" the more quantitative image to the qualitative shape of the on-line or less quantitative image. The resulting remapped image would be more appropriate than either of the planning image or the on-line image for dose calculation or quantitative applications as it would have the quantitative benefits of the first image, but with the updated anatomical information as contained in the second image. This is useful in a variety of cases, such as where the first image (e.g., a planning image) is a CT image and where the second image lacks quantitative image values (e.g., MRI, PET, SPECT, ultrasound, or non-quantitative CT, etc. images). A deformation map also can relate a reference image, such as a 3D image (e.g., a planning image or a pre-treatment image), and a time-based series of images, such as a 4D CT image to determine an amount of radiation dose delivered to the patient 14.

The deformation module 126 can correct for geometrical distortion, imperfections, and/or incompleteness in lieu of, or in addition to, quantitative limitations. For example, a current MRI image that represents anatomy well but includes geometric distortion might be remapped to a CT image that is not distorted. Or, multiple images can be used to simultaneously correct for distortion while representing anatomical changes.

The deformation map can be used to calculate radiation dose on patient images acquired after the planning image. It is also useful to accumulate the doses for multiple delivered fractions. The doses can be added based upon the location of the doses in physical space, but another method is to incorporate deformation methods into the process so as to add doses based upon the structures that received the dose, even if the structures have changed location. The deformation module 126 can calculate the doses of radiation that the patient 14 has received from previously delivered fractions.

While the deformation process above was described in the context of registering one image to another image, it can also work with deformably registering a set of two or more images with another set of one or more images. For example, if there are two pairs of images, each pair comprising an MRI and a CT image, then the deformation map can register the two MRI images together in regions where the MRI has more information, and the CT images together where the CT has more information. These deformations can then be combined. Or deformation maps between the images could be used together, such as for using the CT deformation maps to correct for geometric distortion, imperfections, and/or incompleteness in the MRI images and deformations, and then, having corrected that distortion, imperfections, and/or incompleteness using the MRI deformation maps for better analysis of soft-tissue motion. In a general sense, this process enables imaging improvement via deformation, as poor images can be better understood, and therefore improved, by applying deformation techniques that indicate information like anatomical sizes, shapes, and content. This information can be incorporated into image reconstruction, modification, or enhancement processes.

The software program 90 also includes a treatment delivery module 130 operable to instruct the radiation therapy treatment system 10 to deliver the treatment plan to the patient 14 according to the treatment plan. The treatment delivery module 130 can generate and transmit instructions to the gantry 18, the linear accelerator 26, the modulation device 34, and the drive system 86 to deliver radiation to the patient 14. The instructions coordinate the necessary movements of the gantry 18, the modulation device 34, and the drive system 86 to deliver the radiation beam 30 to the proper target in the proper amount as specified in the treatment plan.

The treatment delivery module 130 also calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 130 can utilize canonical, predetermined or template leaf patterns to generate the appropriate pattern for the radiation beam 30 based on the treatment parameters. The treatment delivery module 130 can also include a library of patterns for typical cases that can be accessed in which to compare the present patient data to determine the pattern for the radiation beam 30.

Figure 5:
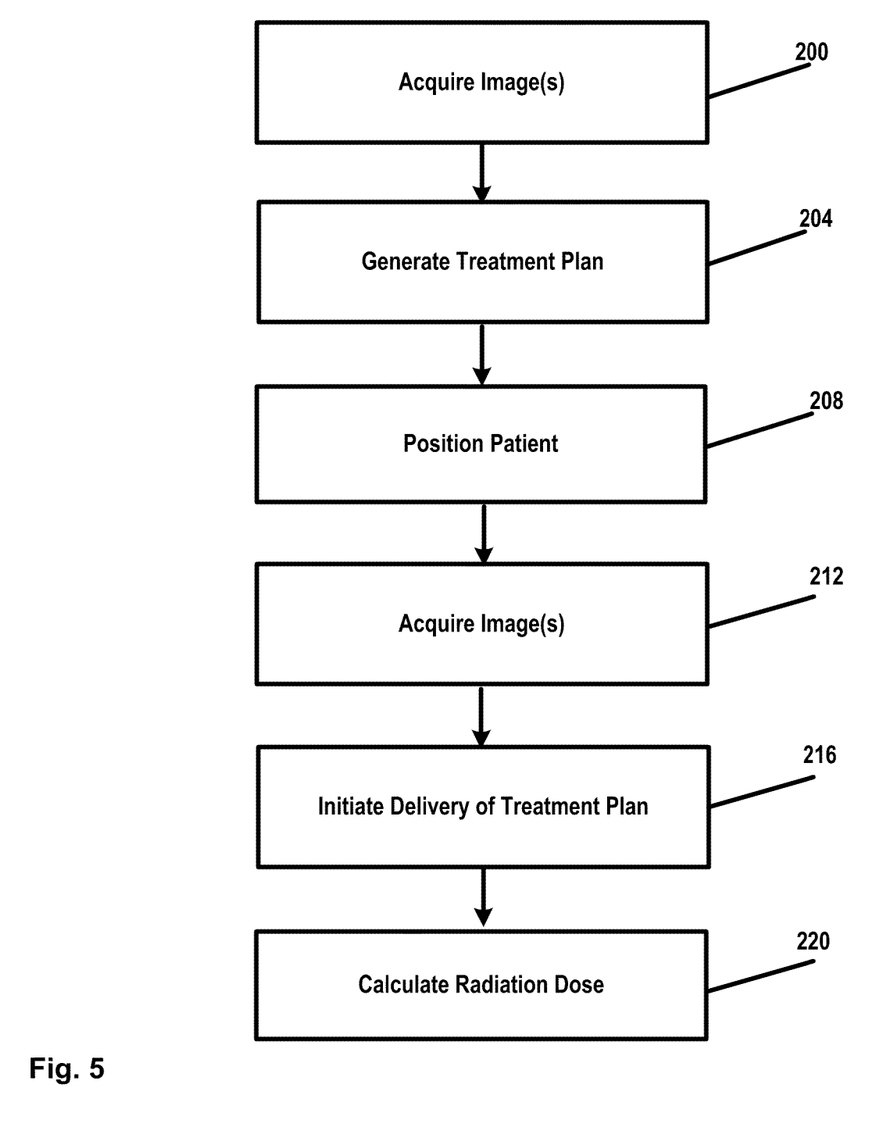
FIG. 5 is a flow chart of a method of automatically processing data relating to a radiation therapy treatment plan according to one embodiment of the present invention.

FIG. 5 illustrates a flow chart of a method of automatically processing data relating to a radiation therapy treatment plan according to one embodiment of the invention. Medical personnel acquire (at 200) image data of the patient to generate (at 204) a treatment plan for the patient 14 based on the image(s), patient data, or other information. The treatment plan includes a radiation dose amount to be delivered to the patient. When the patient 14 is ready for a treatment, medical personnel position (at 208) the patient 14 on the couch 82 with the assistance of the patient positioning module 110 prior to delivery of treatment. Medical personnel initiate (at 212) acquisition of one or more images of the patient 14 while the patient is on the couch 82. After the patient 14 is properly positioned, the medical personnel initiate (at 216) delivery of the treatment plan and radiation dose. The dose calculation module 122 automatically recalculates (at 220) the radiation dose that the patient received.

Figure 6:
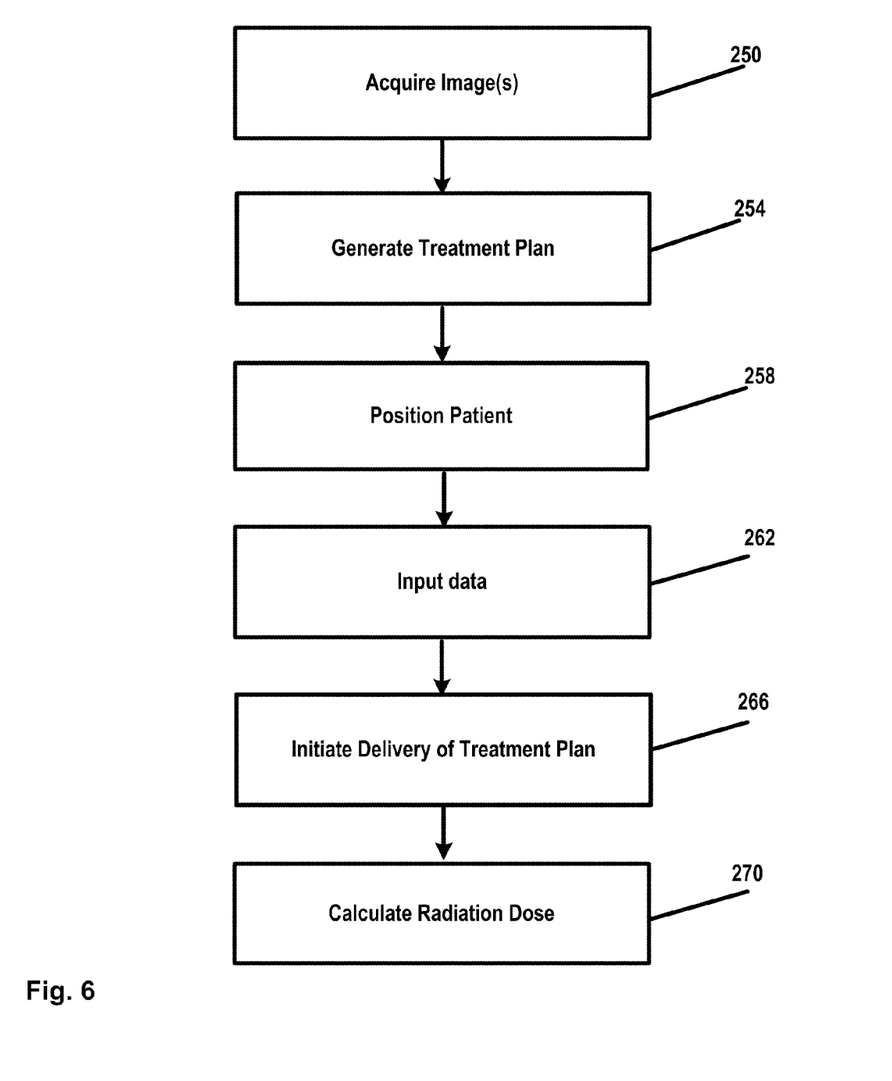
FIG. 6 is a flow chart of a method of automatically processing data relating to a radiation therapy treatment plan according to one embodiment of the present invention.

FIG. 6 illustrates a flow chart of a method of automatically processing data relating to a radiation therapy treatment plan according to one embodiment of the invention. Medical personnel acquire (at 250) image data of the patient to generate (at 254) a treatment plan for the patient 14 based on the image(s), patient data, or other information. The treatment plan includes a radiation dose amount to be delivered to the patient. When the patient 14 is ready for a treatment, medical personnel position (at 258) the patient 14 on the couch 82 with the assistance of the patient positioning module 110 prior to delivery of treatment. Medical personnel may initiate acquisition of one or more images of the patient 14 while the patient is on the couch 82. Prior to delivery of the treatment, medical personnel input (at 262) additional data into the treatment plan module 106 and dose calculation module 126. After the patient 14 is properly positioned, the medical personnel initiate (at 266) delivery of the treatment plan and radiation dose. The dose calculation module 122 automatically recalculates (at 270) the radiation dose that the patient received.

Various features and advantages of the invention are set forth in the following claims.

What is claimed is:

1. A method of automatically processing data relating to a radiation therapy treatment plan, the method comprising:
acquiring image data of a patient;
generating a treatment plan for the patient based at least in part on the image data, the treatment plan including a calculated radiation dose to be delivered to the patient;

acquiring an on-line volumetric image of the patient in substantially a treatment position, the image including sufficient image data to allow calculation of dose;

delivering at least a portion of the calculated radiation dose to the patient; and automatically calculating using a computer the radiation dose using the online volumetric image, the radiation dose reflecting what has been received by the patient.

2. A method as set forth in claim 1 and further comprising automatically performing deformable registration of the image data to accumulate the radiation dose delivered across all images.

3. A method as set forth in claim 2 and further comprising revising the treatment plan in response to the deformable registration.

4. A method as set forth in claim 3 wherein automatically revising the treatment plan further comprises the act of recalculating dose to be delivered in future treatments across all images.

5. A method as set forth in claim 3 wherein the accumulated radiation dose includes delivered radiation doses and future deliveries of radiation doses.

6. A method as set forth in claim 1 and further comprising automatically performing deformable registration of the image data to accumulate predictive radiation doses to be delivered in future treatments.

7. A method as set forth in claim 1 and further comprising automatically displaying a different treatment plan based at least in part on the delivered radiation dose.

8. A method as set forth in claim 7 wherein the different plan is a new plan or a revision of an old plan.

9. A method as set forth in claim 1 and further comprising automatically presenting dosimetric information to a user.

10. A method as set forth in claim 9 and further comprising automatically presenting one of a delivered radiation dose, a planned radiation dose, a comparison of the delivered radiation dose and the planned radiation dose, a gamma function, and a xi function.

11. A method as set forth in claim 1 and further comprising automatically processing images of the patient.

12. A method as set forth in claim 11 wherein the act of automatically processing the images further comprises at least one of merging images, couch replacement, density correction, and application of registration parameters.

13. A method as set forth in claim 1 and further comprising automatically identifying a biological model relating radiation dose delivered to patient effects, and utilizing the biological model to revise the radiation therapy treatment plan.

14. A method as set forth in claim 1 and further comprising defining a software macro to customize at least one automated process.

15. A method as set forth in claim 1 and further comprising automatically identifying a patient treatment parameter falling outside of a defined tolerance, and automatically notifying a user of the violation of the tolerance.

16. A method as set forth in claim 15, wherein the automatic notification occurs via e-mail.

17. A method as set forth in claim 15, wherein the automatic notification occurs via one of a mobile phone and a pager.

18. A method as set forth in claim 1 and further comprising establishing a threshold to determine when automatic replanning occurs.

19. A method as set forth in claim 18 and further comprising stopping treatment based on the threshold.

20. A method as set forth in claim 1 and further comprising generating more than one treatment plan and allowing a user to select one of the plans.

21. A method as set forth in claim 1 and further comprising automatically generating a different treatment plan for the patient based in part on the radiation dose delivered to the patient.

22. A method as set forth in claim 21 wherein the different plan is a new plan or a revision of an old plan.

23. A method as set forth in claim 1 and further comprising automatically replanning based on current anatomy and anticipated anatomy changes of the patient.

24. A method as set forth in claim 1 wherein automatically calculating the radiation dose received by the patient includes incorporating previous dosimetric data from an earlier treatment delivery.

25. A method of automatically processing data relating to a radiation therapy treatment plan, the method comprising:

acquiring volumetric image data of a patient, the image data including sufficient information to allow calculation of dose;

generating a treatment plan for the patient based at least in part on the image data, the treatment plan including a calculated radiation dose to be delivered to the patient;

inputting new data relating to radiation therapy treatment, the data not included in the treatment plan;

delivering at least a portion of the calculated radiation dose to the patient; and automatically calculating using a computer the radiation dose reflecting what has been received by the patient.

26. A method as set forth in claim 25 wherein the new data is one of registration information and setup information for the patient.

27. A method as set forth in claim 25 wherein the new data is acquired during delivery of the treatment plan.

28. A method as set forth in claim 25 wherein the new data is image data.

29. A method as set forth in claim 28 wherein the image data is from a planning image.

30. A method as set forth in claim 28 wherein the image data is from a previous off-line image.

31. A method as set forth in claim 25 wherein the new data is machine-related data.

32. A method as set forth in claim 25 wherein automatically calculating the radiation dose received by the patient includes using one of a planning image, a modified version of the planning image, an image acquired while the patient is substantially in a treatment position, and a combination of images to calculate the radiation dose received by the patient.

33. A system for automatically processing data relating to a radiation therapy treatment plan, the system comprising:

a radiation therapy treatment device including a computer processor, the radiation therapy treatment device operable to deliver radiation to a patient according to a treatment plan; and a software program stored in a computer readable medium accessible by the computer processor, the software being operable to acquire image data of a patient, generate a treatment plan for the patient based at least in part on the image data, the treatment plan including a calculated radiation dose to be delivered to the patient, acquire an on-line volumetric image, including sufficient image data to allow calculation of dose, of the patient in substantially a treatment position, deliver at least a portion of the calculated radiation dose to the patient, and automatically calculate the radiation dose reflecting what has been received by the patient.

34. A system as set forth in claim 33 wherein the software is further operable to automatically perform deformable registration of the image data to accumulate the radiation dose delivered across all images.

35. A system as set forth in claim 34 wherein the software is further operable to revise the treatment plan in response to the deformable registration.

36. A system as set forth in claim 35 wherein the software being operable to automatically revise the treatment plan includes the software is operable to recalculate dose to be delivered in future treatments across all images.

37. A system as set forth in claim 35 wherein the accumulated radiation dose includes delivered radiation doses and future deliveries of radiation doses.

38. A system as set forth in claim 34 wherein the software is further operable to automatically perform deformable registration of the image data to accumulate predictive radiation doses to be delivered in future treatments.

39. A system as set forth in claim 33 wherein the software is further operable to automatically display a different treatment plan based at least in part on the delivered radiation dose.

40. A system as set forth in claim 39 wherein the different plan is a new plan or a revision of an old plan.

41. A system as set forth in claim 33 wherein the software is further operable to automatically present dosimetric information to a user.

42. A system as set forth in claim 41 wherein the software is further operable to automatically present one of a delivered radiation dose, a planned radiation dose, a comparison of the delivered radiation dose and the planned radiation dose, a gamma function, and a xi function.

43. A system as set forth in claim 33 wherein the software is further operable to automatically process images of the patient.

44. A system as set forth in claim 43 wherein the software being operable to automatically process the images includes being operable to merge at least one of images, couch replacement, density correction, and application of registration parameters.

45. A system as set forth in claim 33 wherein the software is further operable to automatically identify a biological model relating radiation dose delivered to patient effects, and utilize the biological model to revise the radiation therapy treatment plan.

46. A system as set forth in claim 33 wherein the software is further operable to define a software macro to customize at least one automated process.

47. A system as set forth in claim 33 wherein the software is further operable to automatically identify a patient treatment parameter falling outside of a defined tolerance, and automatically notify a user of the violation of the tolerance.

48. A system as set forth in claim 47, wherein the automatic notification occurs via e-mail.

49. A system as set forth in claim 47, wherein the automatic notification occurs via one of a mobile phone and a pager.

50. A system as set forth in claim 33 wherein the software is further operable to establish a threshold to determine when automatic replanning occurs.

51. A system as set forth in claim 50 wherein the software is further operable to stop treatment based on the threshold.

52. A system as set forth in claim 33 wherein the software is further operable to generate more than one treatment plan and allow a user to select one of the treatment plans.

53. A system as set forth in claim 33 wherein the software is further operable to automatically generate a different treatment plan for the patient based in part on the radiation dose delivered to the patient.

54. A system as set forth in claim 53 wherein the different plan is a new plan or a revision of an old plan.

55. A system as set forth in claim 33 wherein the software is further operable to automatically replan based on current anatomy and anticipated anatomy changes of the patient.

56. A system as set forth in claim 33 wherein the software being operable to automatically calculate the radiation dose received by the patient includes the software being operable to incorporate previous dosimetric data from an earlier treatment delivery.

* * * * *